(12) United States Patent
Ghelli et al.

(10) Patent No.: US 7,748,438 B2
(45) Date of Patent: Jul. 6, 2010

(54) HEAT EXCHANGE FOR MEDICAL USE

(75) Inventors: Nicola Ghelli, S. Pietro In Casale (IT); Edgardo Costa Maianti, Mirandola (IT); Roberto Balanzoni, San Giovanni del Dosso (IT)

(73) Assignee: Eurosets S.R.L., Medolla (IT)

(*) Notice: Subject to any disclaimer, the term of this patent is extended or adjusted under 35 U.S.C. 154(b) by 695 days.

(21) Appl. No.: 11/526,048

(22) Filed: Sep. 25, 2006

(65) Prior Publication Data

US 2007/0079955 A1    Apr. 12, 2007

(30) Foreign Application Priority Data

Oct. 10, 2005    (IT)   .......................... MI2005A1899

(51) Int. Cl.
    *F28F 1/06* (2006.01)
(52) U.S. Cl. .................. 165/158; 165/162; 165/179
(58) Field of Classification Search ................ 165/158, 165/162, 177, 179, DIG. 417, DIG. 419, 165/DIG. 536
    See application file for complete search history.

(56) References Cited

U.S. PATENT DOCUMENTS

| 2,086,222 | A | | 7/1937 | Karkness |
| 4,056,143 | A | * | 11/1977 | Martin ........................ 165/176 |
| 2003/0173070 | A1 | | 9/2003 | Kamino et al. |
| 2004/0104015 | A1 | * | 6/2004 | O'Donnell et al. ........ 165/109.1 |

FOREIGN PATENT DOCUMENTS

| DE | 26 08 623 A1 | 9/1977 |
| WO | WO 00/25843 A | 5/2000 |

* cited by examiner

*Primary Examiner*—Teresa J Walberg
(74) *Attorney, Agent, or Firm*—Modiano & Associati; Albert Josif; Daniel J. O'Byrne

(57) ABSTRACT

A heat exchanger for medical use, comprising a tube bundle formed by a plurality of tubes having a straight axis for the conveyance of a primary fluid, which are embedded at their ends in disks located at the end faces of an outer jacket which is adapted to delimit, together with the disks, a portion of space for the containment of the tube bundle which is designed to be crossed by a secondary fluid, each tube having, at least at a portion of its length, a plurality of consecutive crimps adapted to determine a progressive variation of the shape of the passage section.

7 Claims, 4 Drawing Sheets

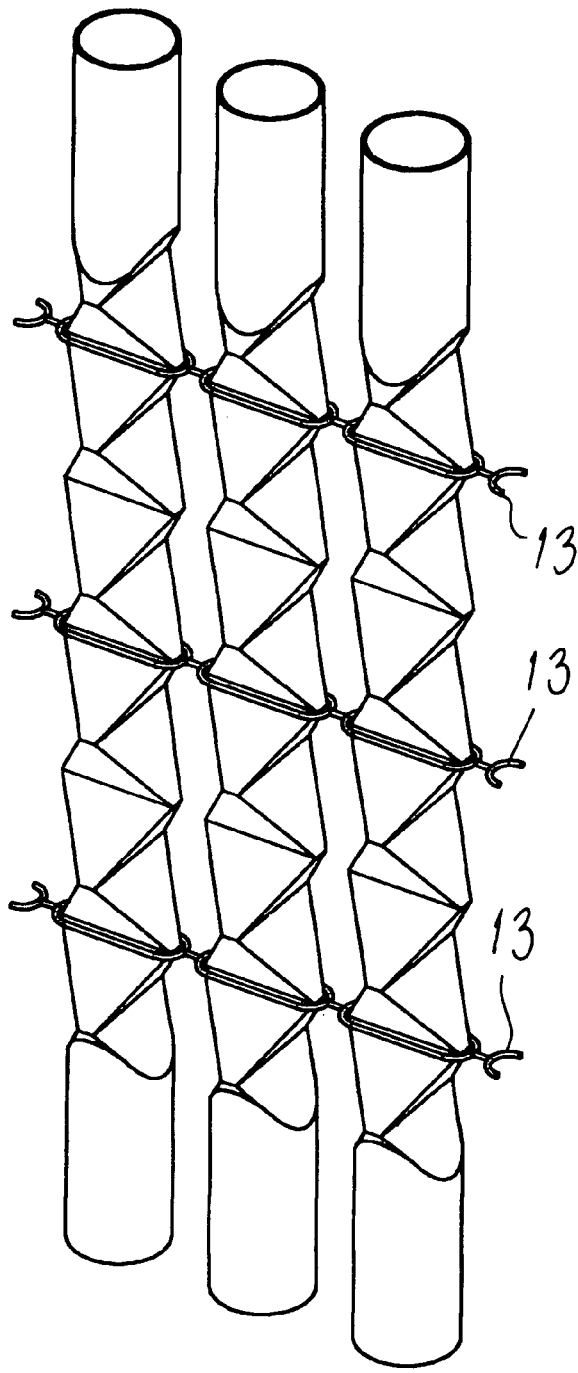
Fig. 9
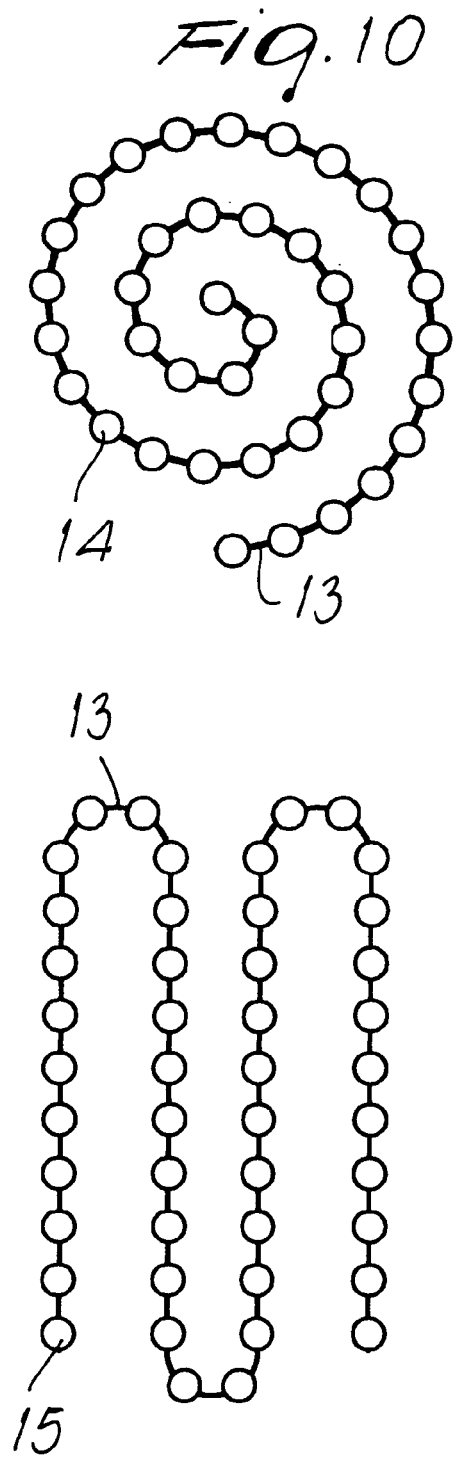
Fig. 10
Fig. 11

HEAT EXCHANGE FOR MEDICAL USE

The present invention relates to a heat exchanger for medical use.

BACKGROUND OF THE INVENTION

It is known that extracorporeal circuits designed to be crossed by blood during certain surgical procedures comprise, among others, a device in which the blood exchanges heat with a fluid, usually water, in order to provide optimum temperature adjustment.

In the medical field there are also many other applications in which a device is provided which is designed to exchange heat between a generic primary fluid and a generic secondary fluid, which are thus not necessarily constituted by blood and water.

Such heat exchanger has different shapes in the background art, and a very common one provides for the presence of a bundle of tubes which comprises a plurality of cylindrical tubes for conveying the primary fluid which are arranged with parallel axes and are embedded at their ends in disks located at the end faces of an external jacket which is adapted to delimit with such disks a portion of space for containing the tube bundle; such portion of space is intended to be crossed by the secondary fluid.

SUMMARY OF THE INVENTION

Such devices certainly have high-level functional characteristics, but the aim of the present invention is to provide a device whose heat exchange efficiency is improved further.

This aim is achieved by a heat exchanger for medical use according to the invention, comprising a tube bundle formed by a plurality of tubes having a straight axis for the conveyance of a primary fluid, which are embedded at their ends in disks located at the end faces of an outer jacket which is adapted to delimit, together with said disks, a portion of space for the containment of said bundle of tubes which is designed to be crossed by a secondary fluid, characterized in that each tube has, at least at a portion of its length, a plurality of consecutive crimps adapted to determine a progressive variation of the shape of the passage section.

BRIEF DESCRIPTION OF THE DRAWINGS

Further characteristics and advantages of the present invention will become better apparent from the description of a preferred but not exclusive embodiment thereof, illustrated by way of non-limiting example in the accompanying drawings, wherein:

FIG. 9 is a view of an embodiment of the connection of the tubes;

FIGS. 10 and 11 are views of different configurations of the tubes which form the tube bundle.

DESCRIPTION OF THE PREFERRED EMBODIMENTS

Figure 1:
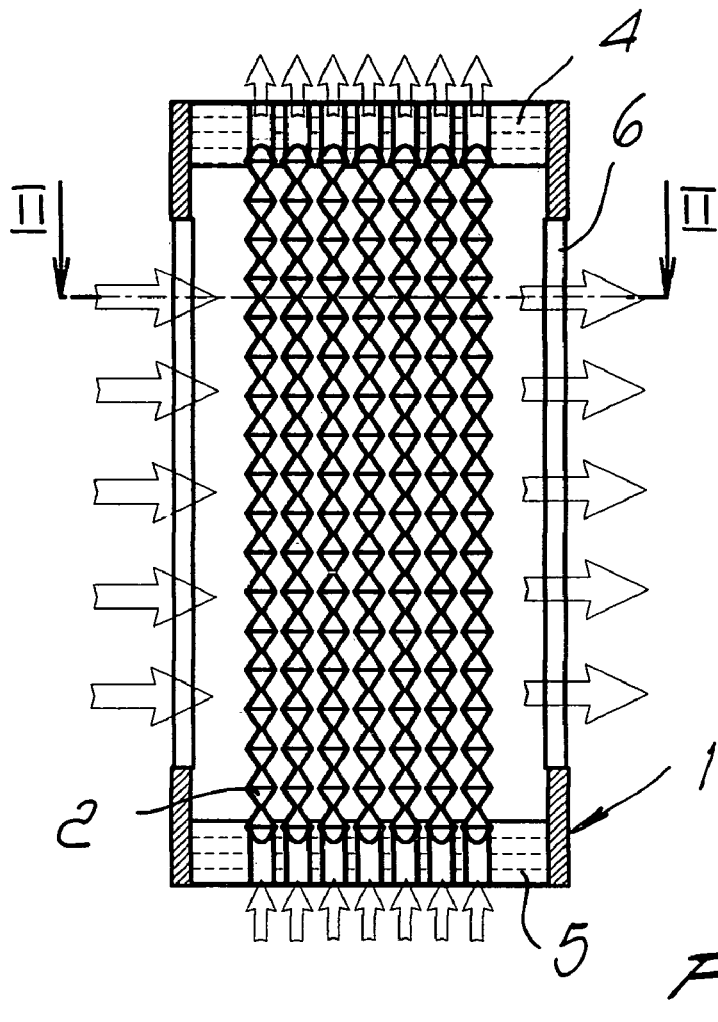
FIG. 1 is a longitudinal sectional view of a heat exchanger according to the invention.
Figure 2:
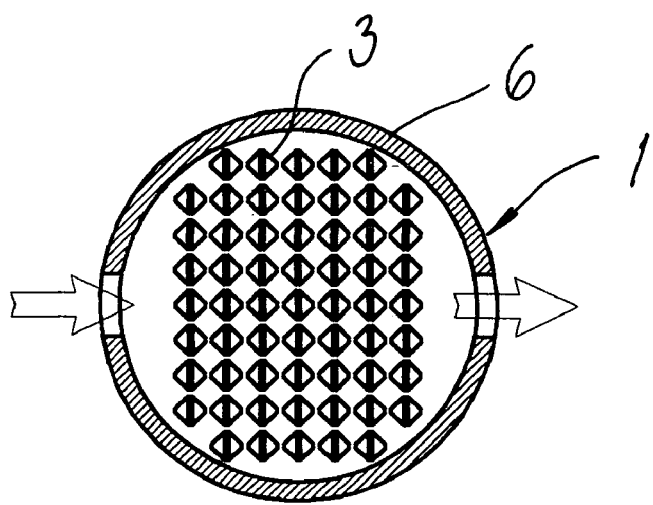
FIG. 2 is a sectional view, taken along the line II-II of FIG. 1.
Figures 3, 4, 5:
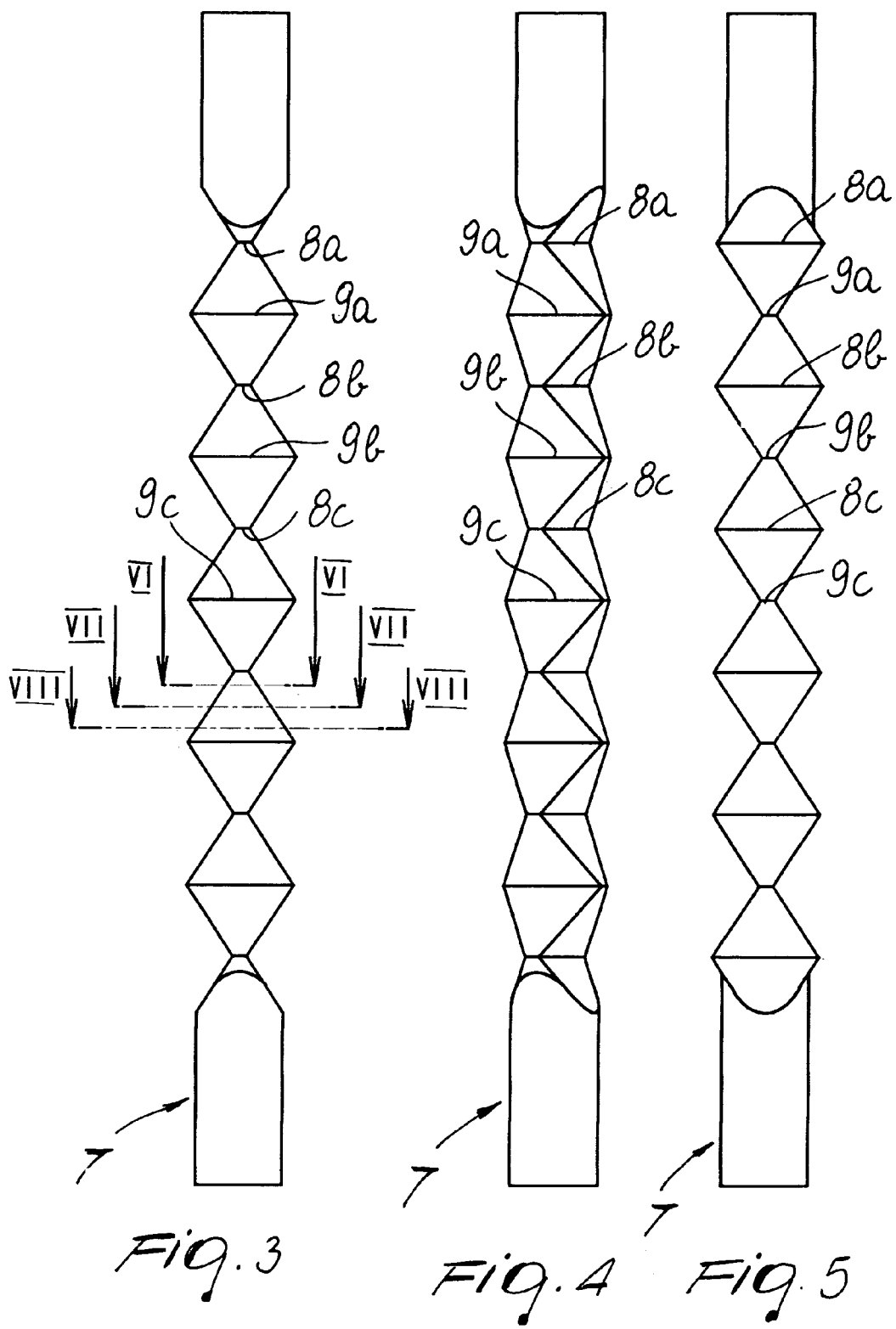
FIGS. 3, 4, 5 are three views of a tube according to the invention obtained by turning such tube with respect to FIG. 3 first through 45° and then through 90°.

With reference to FIGS. 1 and 2, the reference numeral 1 generally designates a heat exchanger according to the invention, which is designed to be inserted in an extracorporeal blood circuit and comprises a tube bundle formed by tubes 2 and 3 for conveying blood, whose axes are straight and parallel; the tubes are embedded at their ends in disks 4 and 5 located at the end faces of an outer jacket 6, which delimits, together with the disks, a portion of space which contains the tube bundle and is designed to be crossed by the fluid for exchanging heat with the blood, constituted by water, along the arrows shown in the figures.

All the tubes 2 and 3 are identical, and therefore a tube according to the invention, generally designated by the reference numeral 7, is described with reference to FIGS. 3 to 8.

Such tube has a plurality of consecutive crimps organized into two series: a first series of parallel crimps 8*a*, 8*b*, 8*c*, which are alternated with parallel crimps 9*a*, 9*b*, 9*c* of a second series, and the directions of the crimps of the two series are mutually offset through 90°.

Each portion of the length of tubes 2, 3, 7, that form a blood passage section, and which is comprised between two consecutive crimps 8*a*, 9*a*; 8*b*, 9*b*, 8*c*, 9*c* is shaped as a prismoid with two opposite faces in which the vertices of the prismoid form opposite quadrilaterals that are joined to each other by trapezoids.

Figure 8:
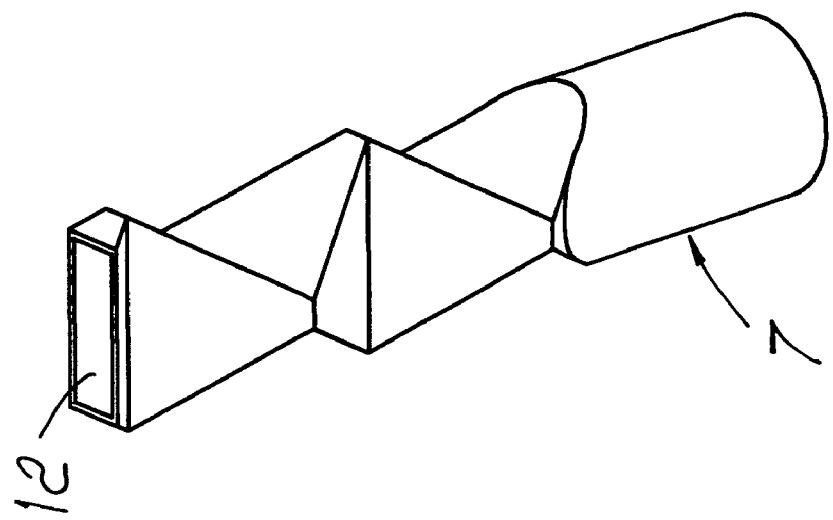
FIGS. 6, 7, 8 are sectional views taken respectively along the lines VI-VI, VII-VII, VIII-VIII of FIG. 3.
Figure 7:
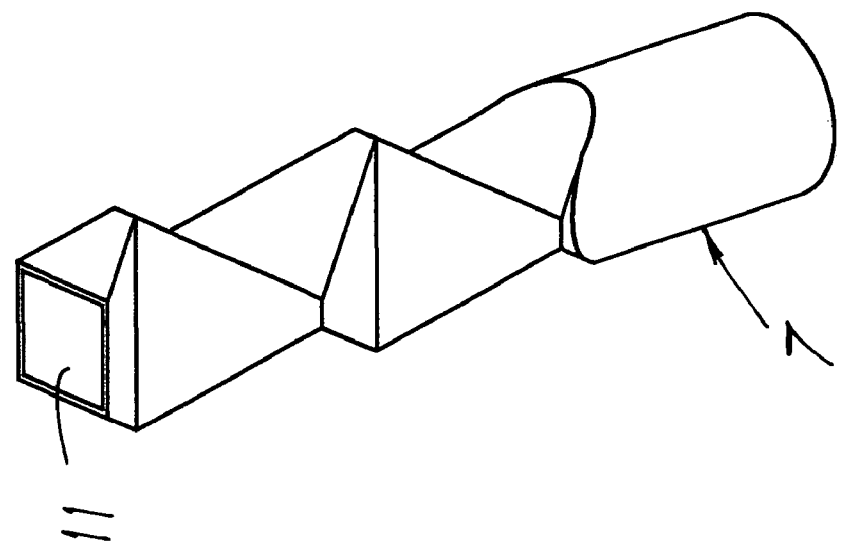
Figure 6:
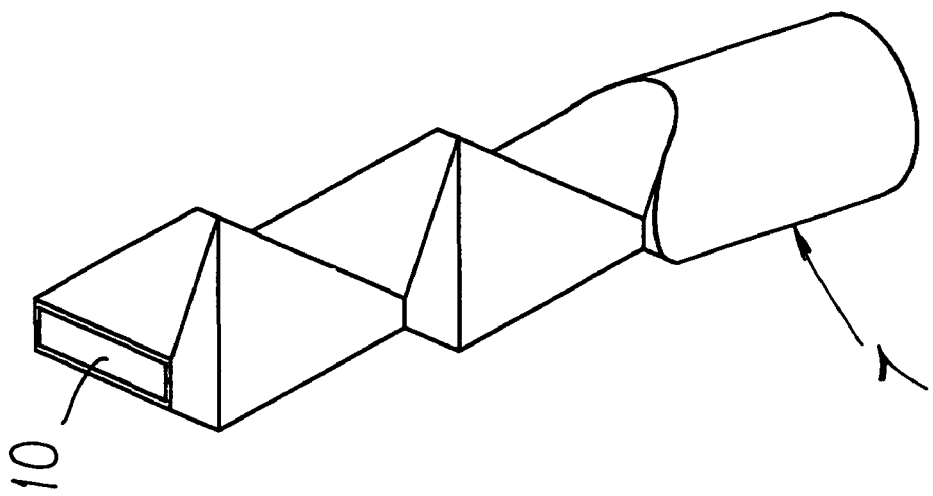

This leads to a progressive variation of the shape of the blood passage section, shown in FIGS. 6, 7, 8 by highlighting cross-sections 10, 11, 12, which induces the blood to move with a turbulent flow, as occurs also for the water as well, with a much higher heat exchange efficiency than that which occurs in known exchangers which use cylindrical tubes, which therefore produce a laminar flow of blood and of the water.

It becomes thus possible to provide compact devices which are highly advantageous in terms of space occupation, of quantity of blood contained, known as priming, and of resistance offered to the flow of the blood.

The device according to the invention can be provided with wire-like elements 13 for connecting one another the individual tubes of the bundle, arranged so as to come into contact with said tubes at coplanar crimps, and thus properly kept in position.

By adopting the wire-like elements 13 it becomes easy to give to the tubes of the tube bundle a prearranged organization, as occurs for tubes 14 of FIG. 10 or tubes 15 of FIG. 11.

The described invention is susceptible of numerous modifications and variations, all of which are within the scope of the appended claims: thus, for example, the directions of the crimps can be offset in any manner and moreover the axes of the tubes, instead of being parallel, may be oblique; moreover, the invention, besides being provided for single use, can be provided with means for coupling to different devices which are integrated in a single structure, as is for example the case of an oxygenation apparatus or of a cardiotomy reservoir used within an extracorporeal blood circuit.

The disclosures in Italian Patent Application No. MI2005A001899 from which this application claims priority are incorporated herein by reference.

What is claimed is:

1. A heat exchanger for medical use, comprising a tube bundle formed by a plurality of tubes having a straight axis for the conveyance of a primary fluid through a passage section thereof, said tubes being embedded at their ends in disks located at the end faces of an outer jacket which is adapted to delimit, together with said disks, a portion of space for the containment of said tube bundle which is designed to be crossed by a secondary fluid, wherein each tube has, at least at a portion of its length, a plurality of consecutive crimps adapted to determine a progressive variation of the shape of the passage section, and wherein each portion of the tube length forming the passage section, and which is comprised between two consecutive ones of said crimps, is shared as a prismoid with two opposite faces in which vertices of the prismoid form opposite quadrilaterals that are joined to each other by trapezoids.

2. The heat exchanger according to claim 1, wherein each tube has a plurality of crimps with mutually offset directions.

3. The heat exchanger according to claim 1, wherein each tube has a first series of parallel crimps alternated with a second series of parallel crimps, said crimps of the two series having directions that are offset.

4. The heat exchanger according to claim 1, wherein each tube has a first series of parallel crimps alternated with a second series of parallel crimps, directions of the crimps of the two series being offset substantially by 90°.

5. The heat exchanger according to claim 1, wherein at least one wire element is provided for mutual connection of the individual tubes of the bundle, arranged so as to come into contact with said tubes at coplanar crimps.

6. The heat exchanger according to claim 1, wherein the tubes of the bundle have parallel axes.

7. A heat exchanger for medical use, comprising:
a tube bundle formed by a plurality of tubes that have straight axes for the conveyance of a primary fluid through a passage section thereof;
an outer jacket;
disks located at end faces of said outer jacket, said outer jacket being adapted to delimit, together with said disks, a portion of space for the containment of said tube bundle which is designed to be crossed by a secondary fluid,
wherein each tube has, at least at a length portion thereof, a plurality of consecutive crimps adapted to determine a progressive variation of the shape of the passage section, each length portion of said tube forming said passage sections and which is comprised between two consecutive ones of said crimps being shaped as a prismoid with two opposite faces in which vertices of the prismoid form opposite quadrilaterals that are joined to each other by trapezoids; and
at least one wire element provided for mutual connection of individual tubes of the bundle, said wire element being arranged so as to come into contact with said tubes at coplanar crimps.

* * * * *